United States Patent
Wang et al.

(10) Patent No.: US 8,269,489 B2
(45) Date of Patent: *Sep. 18, 2012

(54) SYSTEM AND METHOD FOR EDDY CURRENT INSPECTION OF PARTS WITH COMPLEX GEOMETRIES

(75) Inventors: Changting Wang, Niskayuna, NY (US); Yury Alexeyevich Plotnikov, Niskayuna, NY (US); Ui Won Suh, Cincinnati, OH (US); William Stewart McKnight, Hamilton, OH (US)

(73) Assignee: General Electric Company, Niskayuna, NY (US)

( * ) Notice: Subject to any disclaimer, the term of this patent is extended or adjusted under 35 U.S.C. 154(b) by 589 days.

This patent is subject to a terminal disclaimer.

(21) Appl. No.: 12/277,942

(22) Filed: Nov. 25, 2008

(65) Prior Publication Data

US 2010/0127699 A1 May 27, 2010

(51) Int. Cl.
*G01N 27/82* (2006.01)
(52) U.S. Cl. .................................... 324/240
(58) Field of Classification Search .................. 324/237, 324/238, 240
See application file for complete search history.

(56) References Cited

U.S. PATENT DOCUMENTS

| | | | |
|---|---|---|---|
| 4,310,821 A | 1/1982 | Frances | |
| 4,427,940 A * | 1/1984 | Hirama et al. | 324/240 |
| 4,706,020 A | 11/1987 | Viertl et al. | |
| 5,006,800 A | 4/1991 | Hedengren et al. | |
| 5,182,513 A | 1/1993 | Young et al. | |
| 5,237,271 A | 8/1993 | Hedengren | |
| 5,262,722 A | 11/1993 | Hedengren et al. | |
| 5,278,498 A | 1/1994 | Vernon et al. | |
| 5,315,234 A | 5/1994 | Sutton, Jr. et al. | |
| 5,345,514 A | 9/1994 | Mahdavieh et al. | |
| 5,371,461 A | 12/1994 | Hedengren | |
| 5,371,462 A | 12/1994 | Hedengren et al. | |
| 5,389,876 A | 2/1995 | Hedengren et al. | |
| 5,418,457 A | 5/1995 | Hedengren et al. | |
| 5,442,286 A | 8/1995 | Sutton, Jr. et al. | |
| 5,510,709 A | 4/1996 | Hurley et al. | |
| 5,659,248 A | 8/1997 | Hedengren et al. | |
| 5,801,532 A | 9/1998 | Patton et al. | |
| 5,841,277 A | 11/1998 | Hedengren et al. | |
| 5,895,439 A | 4/1999 | Fisher et al. | |
| 5,903,147 A | 5/1999 | Granger, Jr. et al. | |
| 5,966,011 A | 10/1999 | Goldfine et al. | |
| 6,135,627 A | 10/2000 | Beissner et al. | |

(Continued)

OTHER PUBLICATIONS

GE Inspection Technologies; "Aerospace"; Available from Internet:<http://www.geinspectiontechnologies.com/download/applications/GEIT-12002EN_aerospace.pdf>; 16 pages.

(Continued)

*Primary Examiner* — Jay Patidar
*Assistant Examiner* — David M. Schindler
(74) *Attorney, Agent, or Firm* — Penny A. Clarke

(57) ABSTRACT

An inspection system for inspecting a part is provided. The inspection system includes a multi-dimensional array of eddy current sensors that conforms to a contour of a three dimensional shape of the part. The inspection system also includes a controller coupled to the multi-dimensional array, wherein the controller is configured to electronically scan the part via an electrical connection of the eddy current sensors to an eddy current instrument. The inspection system further includes a processor coupled to the eddy current instrument, wherein the processor is configured to analyze output from the eddy current instrument and the controller to accomplish inspection of the part.

12 Claims, 4 Drawing Sheets

U.S. PATENT DOCUMENTS

| | | | |
|---|---|---|---|
| 6,150,809 | A | 11/2000 | Tiernan et al. |
| 6,252,393 | B1 | 6/2001 | Hedengren |
| 6,452,384 | B1 * | 9/2002 | Becker et al. .................. 324/240 |
| 6,504,363 | B1 | 1/2003 | Dogaru et al. |
| 6,608,478 | B1 | 8/2003 | Dziech et al. |
| 6,693,425 | B2 | 2/2004 | Wache |
| 6,707,297 | B2 | 3/2004 | Nath et al. |
| 6,720,775 | B2 | 4/2004 | Plotnikov et al. |
| 6,727,691 | B2 | 4/2004 | Goldfine et al. |
| 6,784,662 | B2 | 8/2004 | Schlicker et al. |
| 6,812,697 | B2 | 11/2004 | McKnight et al. |
| 6,822,443 | B1 | 11/2004 | Dogaru |
| 6,888,346 | B2 | 5/2005 | Wincheski et al. |
| 6,888,347 | B2 | 5/2005 | Batzinger et al. |
| 6,911,826 | B2 | 6/2005 | Plotnikov et al. |
| 6,933,717 | B1 | 8/2005 | Dogaru et al. |
| 6,992,482 | B2 | 1/2006 | Shay et al. |
| 7,015,690 | B2 | 3/2006 | Wang et al. |
| 7,049,811 | B2 | 5/2006 | Schlicker et al. |
| 7,095,224 | B2 | 8/2006 | Goldfine et al. |
| 7,106,055 | B2 | 9/2006 | Goldfine et al. |
| 7,161,351 | B2 | 1/2007 | Goldfine et al. |
| 7,188,532 | B2 | 3/2007 | Goldfine et al. |
| 7,206,706 | B2 | 4/2007 | Wang et al. |
| 2004/0232911 | A1 * | 11/2004 | Schlicker et al. ............. 324/242 |
| 2005/0140366 | A1 * | 6/2005 | Bar et al. ...................... 324/239 |
| 2006/0017434 | A1 | 1/2006 | Tenley et al. |
| 2006/0023961 | A1 | 2/2006 | Suh et al. |
| 2006/0109001 | A1 * | 5/2006 | Suh et al. ...................... 324/232 |
| 2006/0170420 | A1 * | 8/2006 | Nishimizu et al. ............ 324/239 |
| 2006/0290349 | A1 | 12/2006 | Na et al. |
| 2009/0115410 | A1 * | 5/2009 | McKnight et al. ............ 324/240 |

OTHER PUBLICATIONS

"OmniScan Ultrasound, UT Phased Array, eddy current, and EC array"; Available from Internet:<http://wwwenvirocoustics.gr/products/ultrasonic/pdf/OmniScan.pdf>; 14 pages.

Ditchburn, R.J., et al.; Planar Rectangular Spiral Coils in Eddy-Current Non-Destructive Inspection; NDT&E International; pp. 690-700; vol. 38, Issue 8; Dec. 2005.

William Stewart McKnight et al. "Eddy Current Probe and Methods of Assembling the Same"; Pending U.S. Appl. No. 11/935,118, filed Nov. 9, 2007; 32 pages.

* cited by examiner

SYSTEM AND METHOD FOR EDDY CURRENT INSPECTION OF PARTS WITH COMPLEX GEOMETRIES

CROSS REFERENCE TO RELATED APPLICATIONS

This application is related to the following co-pending U.S. patent application Ser. No. 11/935,118, entitled "Eddy Current Probe and Methods of Assembling the Same" assigned to the same assignee as this application, the entirety of which is hereby incorporated by reference herein.

BACKGROUND

The invention relates generally to a system for nondestructive inspection of parts, and more particularly, to a system for detecting flaws in parts employing eddy current method.

The presence of surface cracks and subsurface flaws in metallic structures, such as engine blades, have the potential to lead to failure of an engine. Harsh environment and extreme operating envelope for aircraft engines cause early failures in critical area of engine components. Various inspection methods have been developed and used heretofore for crack and flaw detection with varying degrees of success.

Several prior art inspection methods are deployed for a fine crack detection of aircraft body and engine components. One of methods is fluorescent penetrant inspection (FPI) that applies penetrant material over suspected areas and look for indications with ultraviolet light. The FPI is effective and widely used in aerospace industry and doesn't require stringent inspection environment such as close contact or curvature of parts, but its detectability isn't as good as eddy current inspection. The other is an eddy current inspection that investigates an indication of depth to ascertain crack and flaw severity. The eddy current probes require close proximity to the part. It also requires complex manipulators and inspection plan to follow contoured part geometry to maintain 100% inspection coverage and avoiding lift-off variation between the probes and the. Full coverage with eddy current probes is very time consuming. Spot checking may miss critical crack and defect areas.

Consequently, a need still exists for an improved inspection technique that will provide a solution to the aforementioned problem without introducing any new problems in place thereof.

BRIEF DESCRIPTION

In accordance with one aspect of the invention, an inspection system for inspecting a part is provided. The inspection system includes a multi-dimensional array of eddy current sensors that conforms to a contour of a three dimensional shape of the part. The inspection system also includes a controller coupled to the multi-dimensional array, wherein the controller is configured to electronically scan the part by sequentially connecting sensors in the array to an eddy current instrument. The inspection system further includes a processor coupled to the eddy current instrument, wherein the processor is configured to analyze output from the eddy current instrument and the controller to accomplish inspection of the part.

In accordance with another aspect of the invention, a multi-dimensional array of eddy current sensors that is conformable to a three dimensional shape of a part is provided. The multi-dimensional array of eddy current sensors includes a flexible grid. The multi-dimensional array of eddy current sensors also includes multiple eddy current sensors disposed throughout the flexible grid.

DRAWINGS

These and other features, aspects, and advantages of the present invention will become better understood when the following detailed description is read with reference to the accompanying drawings in which like characters represent like parts throughout the drawings, wherein.

Figure 1:
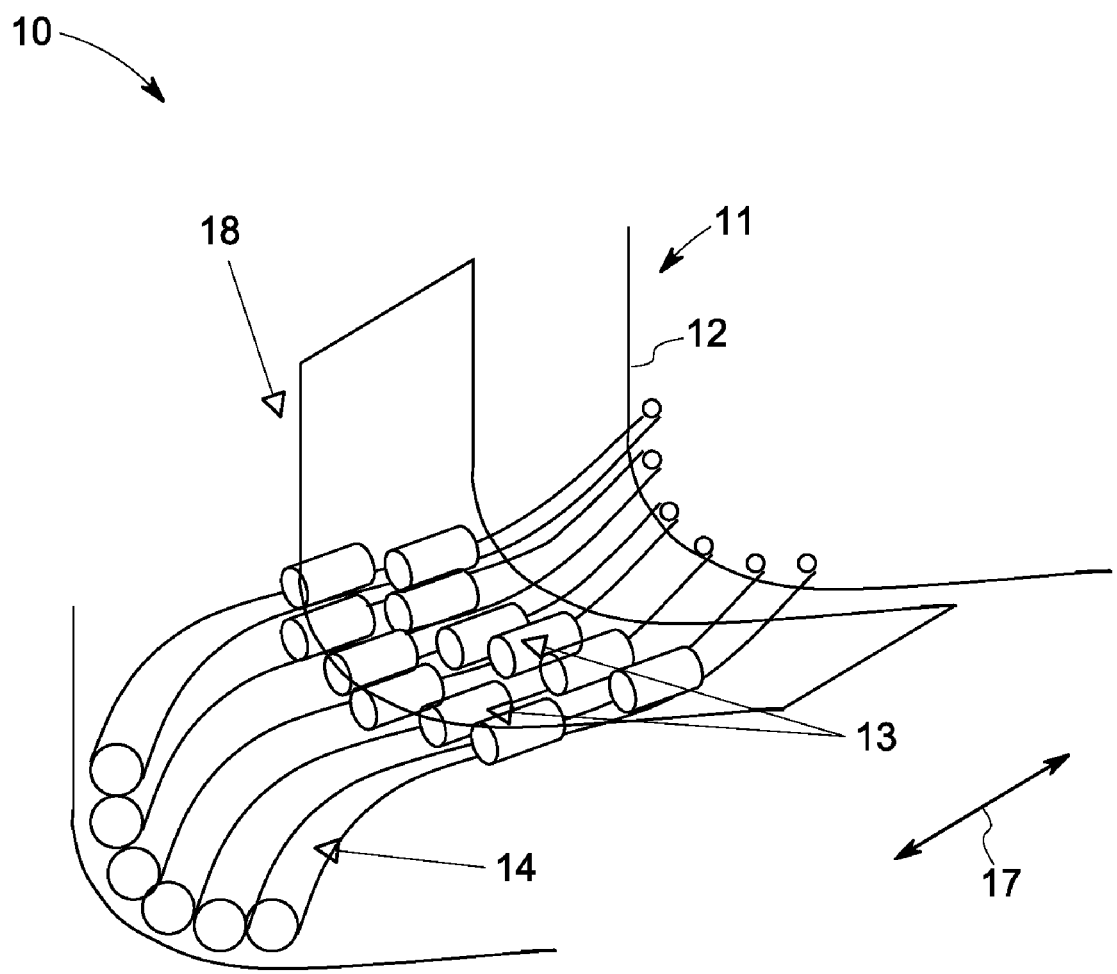
FIG. 1 is a schematic illustration of a multi-dimensional array probe system for inspecting a part having a contoured surface in accordance with an embodiment of the invention.
Figure 5:
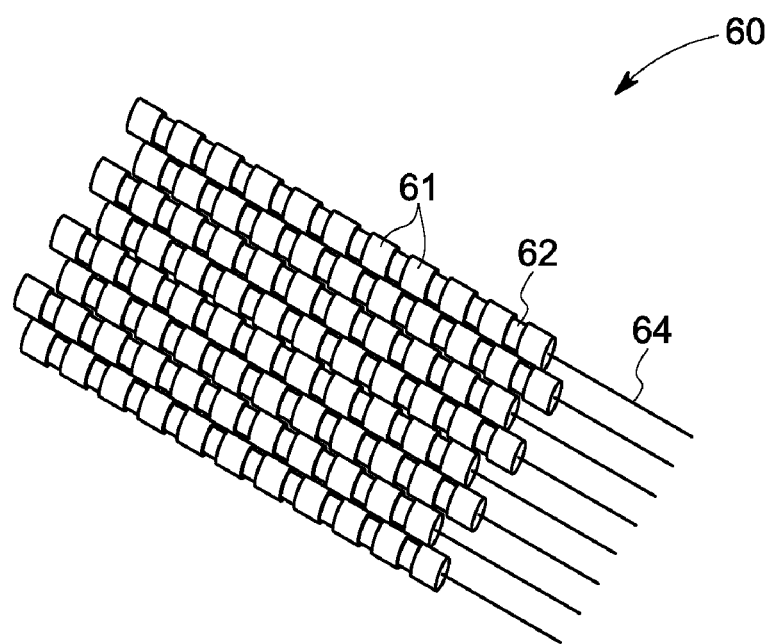
Figure 6:
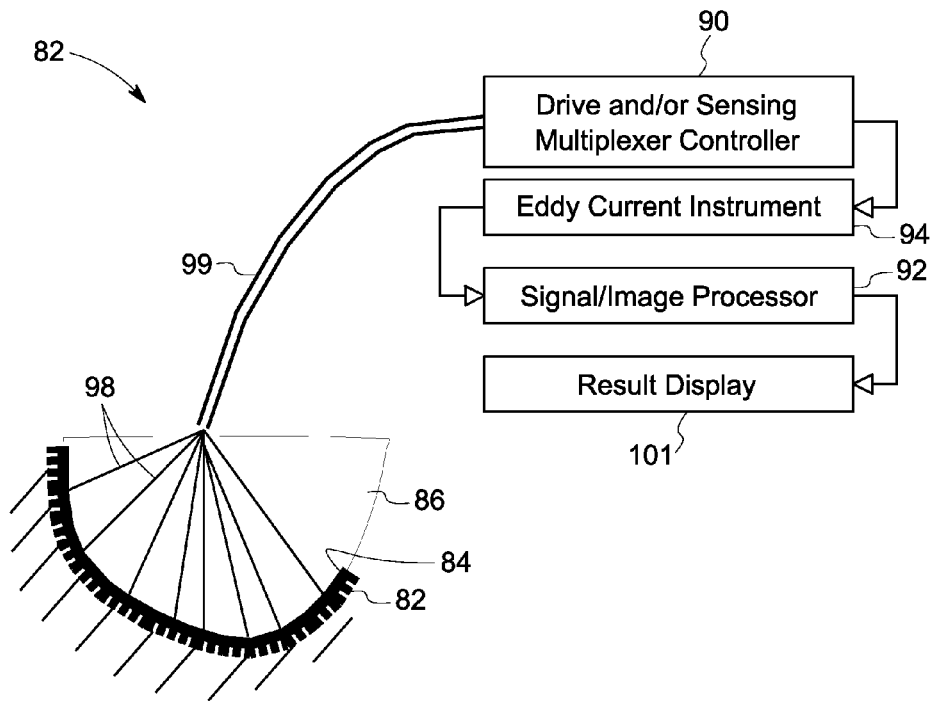
Figure 7:
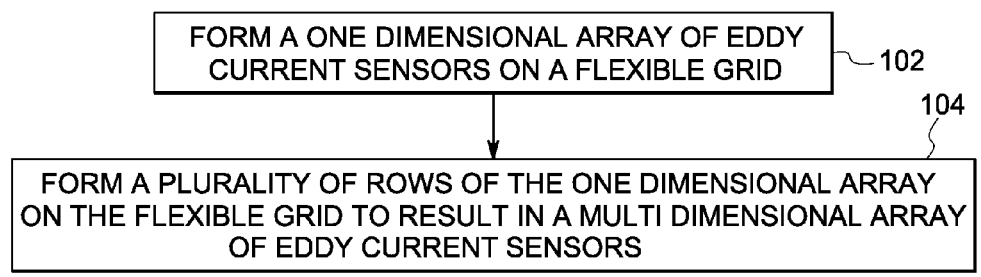

FIG. 5 a diagrammatic illustration of a 2D flexible array of eddy current sensors employing circular flexible tubes in accordance with an embodiment of the invention;

FIG. 6 is a schematic illustration of an inspection system for inspecting a part employing eddy current sensor system in FIG. 1 in accordance with an embodiment of the invention; and FIG. 7 is a flow chart representing steps in a method for forming a multi-dimensional sensor array for use in an inspection system in accordance with an embodiment of the invention.

DETAILED DESCRIPTION

As discussed in detail below, embodiments of the invention are directed to a system and method for inspection of parts with complex geometries. As used herein, the term "inspection" includes inspection for detecting flaws in a complex surface and a sub-surface region of the parts such as, but not limited to, internal cracks, external cracks and pits. A non-limiting example of the part includes an airfoil (turbine blade) in an aircraft engine. It should be appreciated that the methods and apparatus can be applied to a wide variety of components used within an aircraft engine, a steam turbine, a nuclear power plant, an automotive engine, or to inspect any mechanical component.

FIG. 1 is a schematic illustration of a multi-dimensional array probe system 10 for inspecting a part 11 having a contoured surface 12. The system 10 includes a multi-dimensional array of eddy current sensors 13 disposed on a flexible grid 14. The multi-dimensional array of eddy current sensors 13 are arranged such that the array is conformable to a three dimensional shape of the part 11 to be inspected. In one embodiment, the flexible grid 14 includes multiple flexible strands. In the illustrated embodiment, respective coils of the eddy current sensors 13 are wound about respective flexible fibers 14. The flexible fibers enable the eddy current sensors 13 to maintain a substantially uniform contact against the contoured surface 12 as the eddy current sensors 13 are moved across the surface 12 in a scan direction 17.

The flexible grid 14 may be supported by a backing material 18. A non-limiting example of the backing material includes soft durometer backing and shielding. In another embodiment, the grid 14 is non-flexible and the eddy current sensors 13 are interconnected flexibly. In one embodiment, the eddy current sensors may be directly fixed or 'printed' on a 3D surface of the grid 14 that matches a surface of the part to be inspected. In another embodiment, the eddy current sensors 13 include an absolute sensor, a differential, or a pitch-catch sensor. In yet another embodiment, the multi-dimensional array of eddy current sensors is mobile and may be physically scanned.

Figure 2:
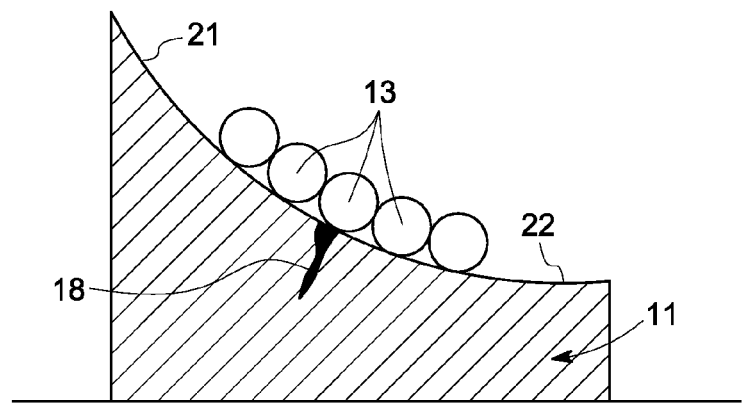
FIG. 2 is a magnified view of the part in FIG. 1 with a contoured surface and a defect.

FIG. 2 is a magnified view of the part 11 with contoured surface 12 and a defect 18. Flexible grid 14 (not shown) enables the sensors 13 to maintain a substantially uniform contact against multiple different contours, such as illustrated at 21 and/or 22 of surface 12 as the sensors 13 are pressed against the surface 12. In one embodiment, coils of the eddy current sensors 13 are disposed tangential to the flexible grid of fibers 14. In an alternative embodiment, coils of the eddy current sensors 13 are disposed normal to the flexible grid of fibers 14.

Figure 3:
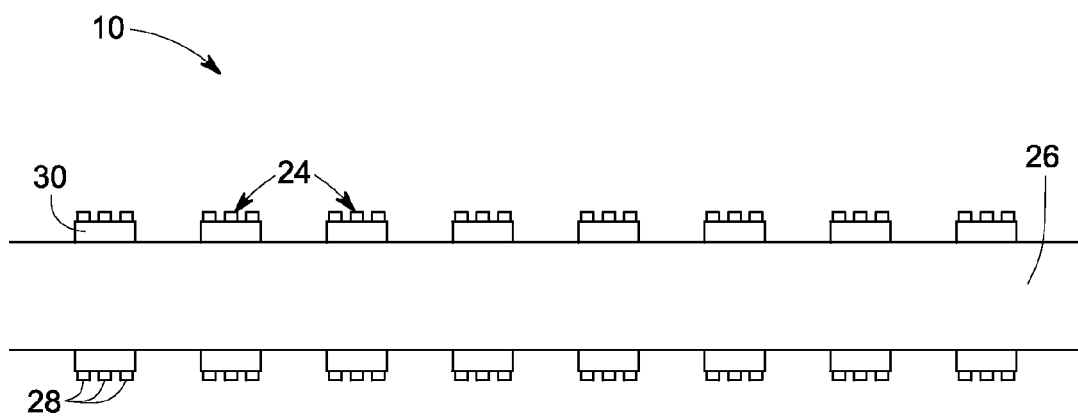
FIG. 3 is a cross-sectional view of an exemplary configuration of the probe system in FIG. 1.

FIG. 3 is a cross-sectional view of an exemplary configuration of the probe system 10 in FIG. 1. The probe system 10 includes multiple eddy current sensors 24, wherein respective ones of the eddy current sensors 24 extend around respective ones of flexible strands 26. Coils 28 are formed on the flexible strands 26 of the eddy current sensors 24 by winding wires around a flexible grid such as, but not limited to, a flexible tube 26. In one embodiment, the eddy current sensors 24 include a magnetic core 30 that extends around respective flexible strands 26 and an eddy current coil 28. At least one eddy current coil 28 is disposed on an outer surface of the magnetic core 30. In an exemplary embodiment, the magnetic core includes a magnetic film such as, but not limited to, ferrite film. The at least one eddy current coil 28 is configurable to be differential or absolute by interconnecting with adjacent coils along one strand or across strands.

Figure 4:
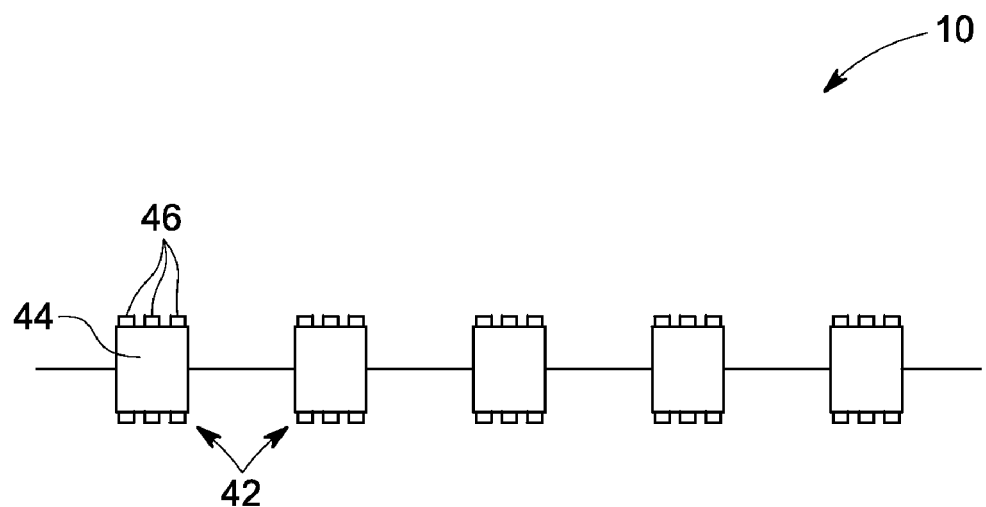
FIG. 4 is a cross-sectional view of another exemplary embodiment of the probe system in FIG. 1.

FIG. 4 is a cross-sectional view of another exemplary embodiment of the probe system 10. The probe system 10 includes eddy current sensors 42 connected adjacent to each other via multiple segments of the flexible strands. In a particular embodiment, each of the eddy current sensors 42 includes a rigid magnetic core 44. A non-limiting example of the magnetic core is a ferrite core. At least one eddy current coil 46 is disposed on an outer surface of the magnetic core 44. Overall flexibility of the probe system 10 is achieved by applying flexible strands connecting multiple magnetic cores 44 into a chain.

FIG. 5 is a diagrammatic illustration of a 2D flexible array 60 of eddy current sensors 61 employing circular flexible tubes 62. Although, the flexible tubes are circular in the illustrated embodiment, the tubes may be rectangular or of any other shape. In a particular embodiment, the electrical connection wires 64 may be disposed through or along the tubes. These wires provide the means of connecting eddy current sensors to the multiplexing controller.

FIG. 6 is a schematic illustration of an inspection system 80 for inspecting a part 82 employing eddy current sensor system 10 in FIG. 1. The inspection system 80 includes a multi-dimensional eddy current sensor array 84 having a contour that is conformable to a three-dimensional shape of the part 82. The array 84 may be supported by a backing material 86. In a particular embodiment, the backing material includes a flexible substrate. In a non-limiting example, the material includes soft durometer. A controller 90 is electrically coupled to the array 84 and is configured to electronically scan the part 82. Furthermore, a processor 92 is coupled to the controller 90. In a particular embodiment, an eddy current instrument 94 is coupled to the controller 90. In the illustrated embodiment, the eddy current instrument 94 is further coupled to the multi-dimensional eddy current sensor array 84, wherein the eddy current instrument is configured to apply multiple excitation signals to respective ones of the sensors in the multi-dimensional eddy current sensor array 84 to generate a number of response signals. The processor 92 analyzes the response signals from the eddy current instrument 94 to inspect the region of interest within the internal cavity of the part. Electrodes or connectors 98 are employed to facilitate electrical connection via electrical cable 99 between the array 84 and the controller 90. In one embodiment, the connectors 98 are passed through the backing material 86.

It is desirable for the eddy current signal due to the flaws to have a signal-to-noise ratio large enough to be detected in a response signal over background noise. Multi-frequency phase analysis enables achieving such signal-to-noise ratio. Further details of the multi frequency phase analysis may be obtained in U.S. Pat. No. 7,206,706 to Wang et al., entitled "Inspection of Non-planar Parts using Multifrequency Eddy Current with Phase Analysis" and assigned to the same assignee of the present invention, which is hereby incorporated herein by reference. Several compensation algorithms may be applied in the signal processing to reduce the sensitivity variation for different defect locations under the sensor array. Examples of the compensation algorithm include, but not limit to, using averaging or root mean square of adjacent channels. A display monitor 101 may be coupled to the processor 92 to display an indication of a presence of at least one flaw in the part 82 based upon the plurality of eddy current signals. It is possible that the controller and/or the processor and/or the display can be built on the probe body using miniature design within the space limit.

It should be noted that embodiments of the invention are not limited to any particular processor for performing the processing tasks of the invention. The term "processor," as that term is used herein, is intended to denote any device capable of performing the calculations, or computations, necessary to perform the tasks of the invention. The device is capable of accepting a structured input and of processing the input in accordance with prescribed rules to produce an output. It should also be noted that the phrase "configured to" as used herein means that the processor is equipped with a combination of hardware and software for performing the tasks of the invention, as will be understood by those skilled in the art.

FIG. 7 is a flow chart representing steps in a method for forming a multi-dimensional sensor array in an inspection system. The method includes forming a one dimensional array of eddy current sensor coils on a substrate in step 102. In one embodiment, the forming includes disposing the eddy current sensor coils on a flexible substrate. Multiple rows of the one dimensional array are formed in step 104 that result in a multi-dimensional array of eddy current sensor coils such that a contour of the multi dimensional array conforms to a three dimensional shape of a part being tested.

The various embodiments of a system and method for inspection of parts described above thus provide a way to enable inspection of a complex, contoured surface with high productivity. The system and method also reduce rework and reinspection caused by false calls, and improve first time yield. Furthermore, the technique provides an efficient and cost effective means for inspection. The system also allows for inspection of quality of new parts as well as parts that have been in-service to prevent critical part failures. A specific arrangement of the eddy current sensors also allow for full coverage of an inspection area.

Of course, it is to be understood that not necessarily all such objects or advantages described above may be achieved in accordance with any particular embodiment. Thus, for example, those skilled in the art will recognize that the systems and techniques described herein may be embodied or carried out in a manner that achieves or optimizes one advantage or group of advantages as taught herein without necessarily achieving other objects or advantages as may be taught or suggested herein.

Furthermore, the skilled artisan will recognize the interchangeability of various features from different embodiments. For example, the use of a circular flexible tube described with respect to one embodiment can be adapted for use with a soft durometer backing material described with respect to another. Similarly, the various features described, as well as other known equivalents for each feature, can be mixed and matched by one of ordinary skill in this art to construct additional systems and techniques in accordance with principles of this disclosure.

While only certain features of the invention have been illustrated and described herein, many modifications and changes will occur to those skilled in the art. It is, therefore, to be understood that the appended claims are intended to cover all such modifications and changes as fall within the true spirit of the invention.

The invention claimed is:

1. An inspection system for inspecting a part, the inspection system comprising:
    a multi-dimensional array of eddy current sensors that conforms to a contour of a three dimensional shape of the part;
    a controller coupled to the multi-dimensional array, the controller configured to electronically scan the part via an electrical connection of the eddy current sensors to an eddy current instrument; and
    a processor coupled to the eddy current instrument, the processor configured to analyze output from the eddy current instrument and the controller to accomplish inspection of the part,
    wherein the multi-dimensional array of eddy current sensors comprises:
        a flexible grid comprising a plurality of flexible strands, and
        a plurality of eddy current sensors which are disposed throughout and mounted on the flexible grid, wherein respective ones of the plurality of eddy current sensors extend around respective ones of the flexible strands, and wherein each of the plurality of eddy current sensors comprises:
            a magnetic core that extends around one of the respective flexible strand strands; and
            at least one eddy current coil disposed on an outer surface of the magnetic core.

2. The inspection system of claim 1, wherein the magnetic core comprises a magnetic film.

3. The inspection system of claim 1, wherein adjacent ones of the plurality of eddy current sensors are connected via one or more segments of the flexible strands.

4. The inspection system of claim 1, further comprising a backing material, wherein at least a portion of the flexible grid is supported by the backing material.

5. The inspection system of claim 4, wherein the backing material comprises a flexible substrate.

6. The inspection system of claim 1, wherein the multi-dimensional array of eddy current sensors is either stationary or mobile.

7. An inspection system for inspecting a part, the inspection system comprising:
    a multi-dimensional sensor array that is conformable to a three dimensional shape of a part, the multi-dimensional sensor array comprising:
        a flexible grid comprising a plurality of flexible strands; and
        a plurality of eddy current sensors disposed throughout and mounted on the flexible grid, wherein respective ones of the plurality of eddy current sensors extend around respective ones of the flexible strands, and wherein each of the plurality of eddy current sensors comprises:
            a magnetic core that extends around one of the flexible strands; and
            at least one eddy current coil disposed on an outer surface of the magnetic core.

8. The inspection system of claim 7, wherein the magnetic core comprises a magnetic film.

9. The inspection system of claim 7, wherein adjacent ones of the eddy current sensors are connected via one or more segments of the flexible strands.

10. The inspection system of claim 7, further comprising a backing material, wherein at least a portion of the flexible grid is supported by the backing material.

11. The inspection system of claim 10, wherein the backing material comprises a flexible substrate.

12. The inspection system of claim 7, wherein at least one of the plurality of eddy current sensors is selected from the group consisting of an absolute sensor, a differential sensor, and a pitch-catch sensor.

* * * * *

UNITED STATES PATENT AND TRADEMARK OFFICE
CERTIFICATE OF CORRECTION

PATENT NO. : 8,269,489 B2
APPLICATION NO. : 12/277942
DATED : September 18, 2012
INVENTOR(S) : Wang et al.

It is certified that error appears in the above-identified patent and that said Letters Patent is hereby corrected as shown below:

In Column 5, Lines 46-47, in Claim 1, delete "respective flexible strand strands;" and insert
-- flexible strands; --, therefor.

Signed and Sealed this
Twelfth Day of March, 2013

Teresa Stanek Rea
*Acting Director of the United States Patent and Trademark Office*